(12) United States Patent
Lei et al.

(10) Patent No.: US 9,401,659 B2
(45) Date of Patent: Jul. 26, 2016

(54) HIGH VOLTAGE ANALOG SWITCH (71) Applicants: Jimes Lei, Milpitas, CA (US); Kee Chee Tiew, Mountain View, CA (US)

(72) Inventors: Jimes Lei, Milpitas, CA (US); Kee Chee Tiew, Mountain View, CA (US)

(73) Assignee: Monolithic Power Systems, Inc., San Jose, CA (US)

( * ) Notice: Subject to any disclaimer, the term of this patent is extended or adjusted under 35 U.S.C. 154(b) by 0 days.

(21) Appl. No.: 14/563,675

(22) Filed: Dec. 8, 2014

(65) Prior Publication Data

US 2016/0134199 A1  May 12, 2016

Related U.S. Application Data (60) Provisional application No. 62/078,758, filed on Nov. 12, 2014.

(51) Int. Cl.
*H03K 17/687* (2006.01)
*H02M 7/217* (2006.01)
*A61B 8/00* (2006.01)
*G01S 7/52* (2006.01)

(52) U.S. Cl.
CPC ............... *H02M 7/217* (2013.01); *A61B 8/54* (2013.01); *G01S 7/52017* (2013.01)

(58) Field of Classification Search
CPC ................ H01L 2924/00; G09G 2300/0861; G09G 2300/0819; G09G 2300/0842
See application file for complete search history.

(56) References Cited

U.S. PATENT DOCUMENTS

| 8,212,604 | B2 * | 7/2012 | Dianbo | H03K 17/063 327/389 |
|---|---|---|---|---|
| 8,956,375 | B2 | 2/2015 | Nita et al. | |
| 8,961,404 | B2 | 2/2015 | Ito | |
| 8,961,421 | B2 | 2/2015 | Wodnicki | |
| 8,961,423 | B2 | 2/2015 | Nita et al. | |
| 8,961,424 | B2 | 2/2015 | Sato et al. | |
| 8,974,388 | B2 | 3/2015 | Osaka et al. | |
| 8,979,775 | B2 | 3/2015 | Schafer et al. | |
| 2005/0228284 | A1 * | 10/2005 | Baumgartner | A61B 5/6844 600/459 |
| 2011/0037524 | A1 * | 2/2011 | Dao | H03B 5/362 331/47 |
| 2014/0125402 | A1 * | 5/2014 | Chen | H03K 17/693 327/427 |

* cited by examiner

*Primary Examiner* — Sibin Chen
(74) *Attorney, Agent, or Firm* — Okamoto & Benedicto LLP (57) ABSTRACT A high voltage analog switch can be used in medical ultrasound applications. The high voltage analog switch can pass high voltage transducer excitation signals without necessarily having any high voltage power supplies. The high voltage analog switch can include three output switches, with one of the output switches having a clamp circuit for ensuring that transistors of an output switch on an input end of the high voltage analog switch remain OFF when the high voltage analog switch is OFF.

17 Claims, 5 Drawing Sheets

HIGH VOLTAGE ANALOG SWITCH

CROSS-REFERENCE TO RELATED APPLICATION

This application claims the benefit of U.S. Provisional Application No. 62/078,758, filed on Nov. 12, 2014, which is incorporated herein by reference in its entirety.

BACKGROUND OF THE INVENTION

1. Field of the Invention

The present invention relates generally to high voltage analog switches, and more particularly but not exclusively to analog switches used in medical ultrasound applications.

2. Description of the Background Art

High voltage analog switches are employed in medical ultrasound applications to multiplex transmitter and receiver circuits to selected piezoelectric transducers. An analog switch in medical ultrasound applications must be capable of passing high voltage because a piezoelectric excitation signal is in the order of +/−100V (i.e., 200V peak-to-peak). Accordingly, currently available high voltage analog switches employed in medical ultrasound applications are relatively complicated and require one or more high voltage power supplies. The high voltage power supplies not only increase the cost of the medical ultrasound device but also raise safety issues.

SUMMARY

In one embodiment, a high voltage analog switch can be used in medical ultrasound applications. The high voltage analog switch can pass high voltage transducer excitation signals without necessarily having a high voltage power supply. The high voltage analog switch can include three output switches, with one of the output switches having a clamp circuit for ensuring that transistors of an output switch on an input end of the high voltage analog switch remain OFF when the high voltage analog switch is OFF.

These and other features of the present invention will be readily apparent to persons of ordinary skill in the art upon reading the entirety of this disclosure, which includes the accompanying drawings and claims.

DESCRIPTION OF THE DRAWINGS

The use of the same reference label in different drawings indicates the same or like components.

DETAILED DESCRIPTION

In the present disclosure, numerous specific details are provided, such as examples of electrical circuits, components, and methods, to provide a thorough understanding of embodiments of the invention. Persons of ordinary skill in the art will recognize, however, that the invention can be practiced without one or more of the specific details. In other instances, well-known details are not shown or described to avoid obscuring aspects of the invention.

Figure 1:
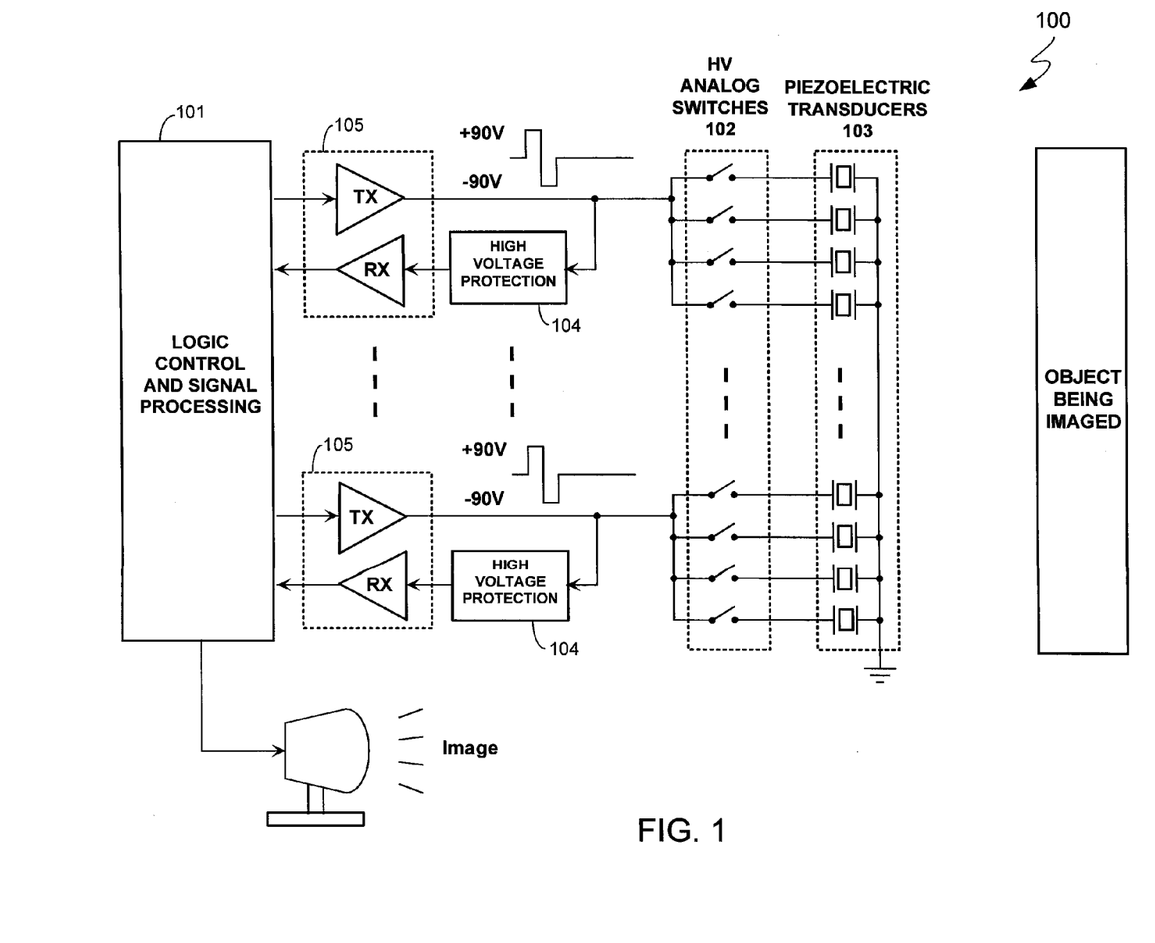
FIG. 1 shows a block diagram of a medical ultrasound device in accordance with an embodiment of the present invention.

FIG. 1 shows a block diagram of a medical ultrasound device 100 in accordance with an embodiment of the present invention. The medical ultrasound device 100 may be portable, cart-based, or have other form factor. In the example of FIG. 1, the medical ultrasound device 100 comprises a plurality of transmitters TX and receivers RX, a plurality of high voltage analog switches 102, and a plurality of piezoelectric transducers 103. A transmitter/receiver pair 105 comprises a transmitter TX for transmitting a transducer excitation signal and a receiver RX for receiving a corresponding return signal, which can comprise an echo from an object being imaged.

A transmitter/receiver pair 105 can be multiplexed by the high voltage analog switches 102 to one of the piezoelectric transducers 103. In the example of FIG. 1, the high voltage analog switches 102 are configured to provide 1 to 4 multiplexing for a transducer excitation signal that swings +/−90V (i.e., 180V peak-to-peak). That is, one transmitter/receiver pair 105 can be connected to one of four piezoelectric transducers 103, with the one piezoelectric transducer 103 being connected to the one transmitter/receiver pair 105 by one high voltage analog switch 102. A piezoelectric transducer 103 can be selected by switching ON its corresponding high voltage analog switch 102 and switching OFF the remaining three high voltage analog switches 102. The multiplexing ratio and the particulars of the transducer excitation signal can vary without detracting from the merits of the present invention. A high voltage analog switch 102 can have a first end node coupled to a transmitter/receiver pair 105 and a second end node coupled to a piezoelectric transducer 103.

In the example of FIG. 1, the medical ultrasound device 100 includes a logic control and signal processing circuit 101 that sends transducer excitation signals to the piezoelectric transducers 103. A transducer excitation signal is transmitted by a transmitter TX to a high voltage analog switch 102, which when ON allows the transducer excitation signal to reach and excite a piezoelectric transducer 103. A high voltage protection circuit 104 protects the corresponding receiver RX from the transducer excitation signal, which is high voltage. An excited piezoelectric transducer 103 emits an acoustic wave towards the object being imaged. The resulting echo from the object is received by the piezoelectric transducer 103 and passes through the high voltage analog switch 102 and onto the receiver RX. An echo signal is relatively weak, which may be in the order of +/−100 μV to +/−100 mV. The logic control and signal processing circuit 101 receives and processes echo signals to construct an image of the object.

Figure 2:
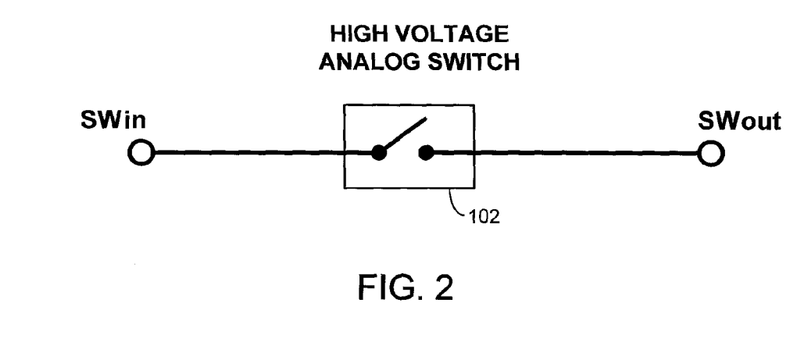
FIGS. 2-4 show schematic diagrams of a high voltage analog switch in accordance with an embodiment of the present invention.

FIG. 2 shows a schematic diagram of a high voltage analog switch 102 in accordance with an embodiment of the present invention. As can be appreciated, the medical ultrasound device 100 has a plurality of high voltage analog switches 102, but only one is shown in FIG. 2 and the following figures for clarity of illustration. A high voltage analog switch 102 can include a first end node SWin and a second end node SWout. As employed in the medical ultrasound device 100 of FIG. 1, the end node SWin can be connected to a transmitter/receiver pair 105 and the end node SWout can be connected to a piezoelectric transducer 103.

Figure 3:
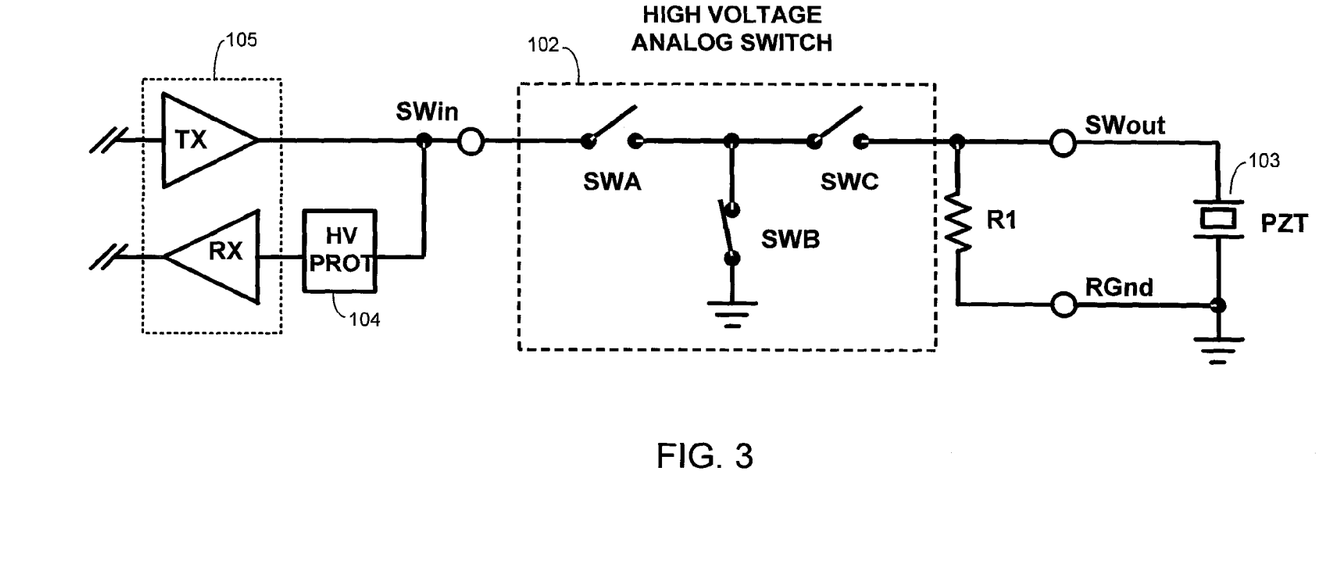

FIG. 3 shows further details of a high voltage analog switch 102 in accordance with an embodiment of the present invention. In the example of FIG. 3, the high voltage analog switch 102 includes three external nodes, which are the end nodes SWin and SWout and a ground node RGnd. In the example of FIG. 3, a bleed resistor R1 connects the end node SWout to the ground node RGnd; a piezoelectric transducer ("PZT") 103 has a node coupled to the end node SWout and an opposing node coupled to the ground node RGnd. FIG. 3 also shows the end node SWin coupled to the output of the transmitter TX and to the input of the receiver RX of a transmitter/receiver pair 105. A high voltage protection circuit 104 protects the input of the receiver RX from a high voltage transducer excitation signal on the end node SWin.

In medical ultrasound applications, the primary purpose of a high voltage analog switch 102 is to multiplex the transmitter TX and receiver RX circuits to selected piezoelectric transducers 103. The transducer excitation signal from a transmitter TX can have high voltage pulses in the order of +/−100V with a frequency range of 1.0 MHz to 15 MHz. Accordingly, a high voltage analog switch 102 needs to be able to pass or block high voltage signals, which can be at least +/−40V (i.e., at least 80V peak to peak) for medical ultrasound applications.

In the example of the FIG. 3, the high voltage analog switch 102 comprises exactly three output switches, namely switches SWA, SWB, and SWC. When the high voltage analog switch 102 is ON, the output switches SWA and SWC are closed and the output switch SWB is open. A transducer excitation signal comprising high voltage pulses passes through the closed output switches SWA and SWC to excite the piezoelectric transducer 103.

When the high voltage analog switch 102 is OFF, the output switches SWA and SWC are open and the output switch SWB is closed. The high voltage pulses cannot pass because the output switch SWA is open. Parasitic capacitance can be coupled across the two terminals of the output switch SWA, allowing some AC (alternating current) current to feed through the output switch SWA. The output switch SWB is closed to shunt the feed-through current to ground. The ON-resistance of the output switch SWB multiplied by the AC current will generate a relatively small AC voltage across the output switch SWB. The small AC voltage across the output switch SWB has a small amplitude but is still enough to excite the piezoelectric transducer 103. To prevent this, the output switch SWC is opened to block the small AC voltage from getting to the piezoelectric transducer 103.

Figure 4:
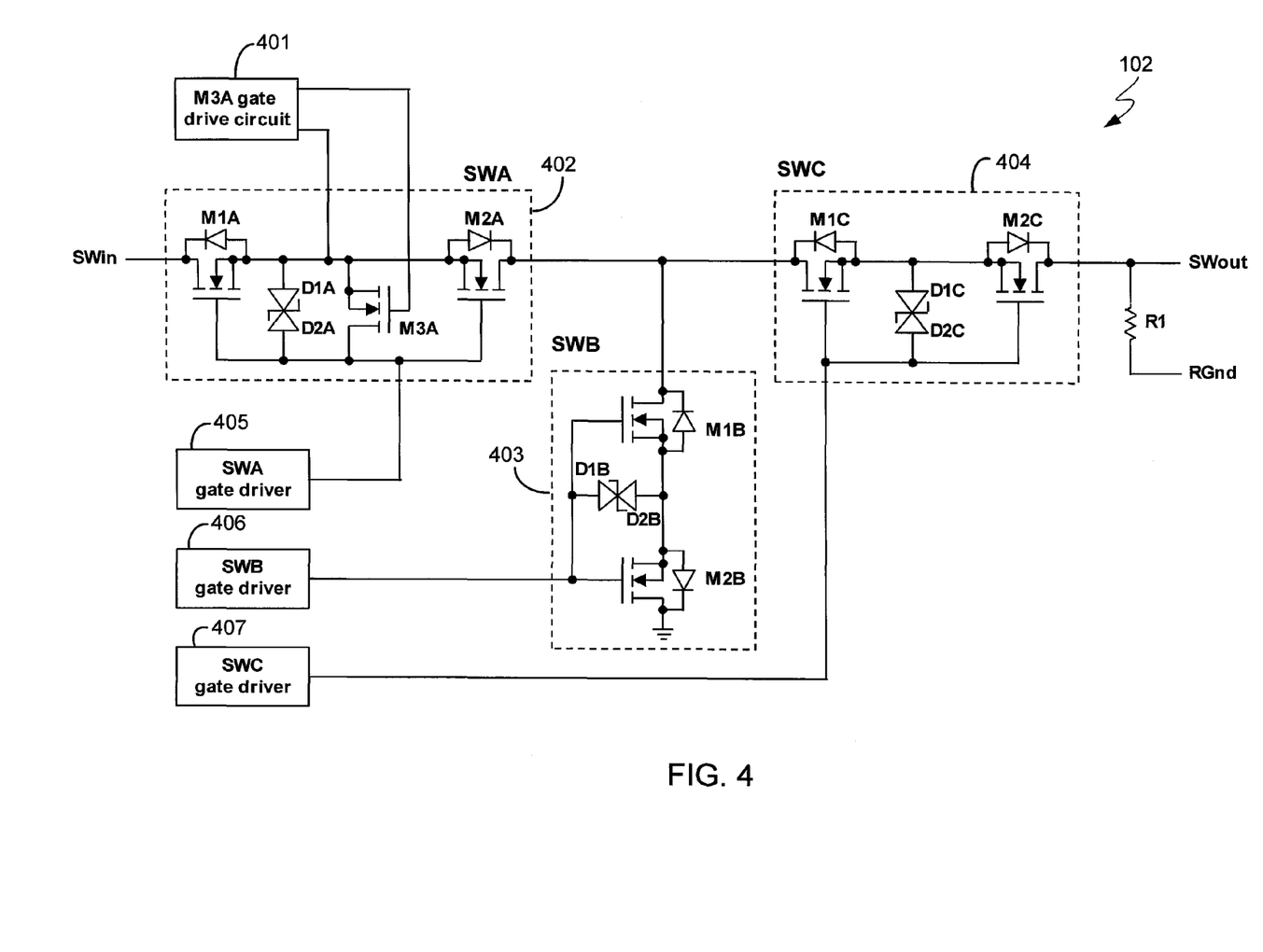

FIG. 4 shows further details of a high voltage analog switch 102 in accordance with an embodiment of the present invention. In the example of FIG. 4, the high voltage analog switch 102 comprises the output switches SWA (labeled as 402), SWB (labeled as 403), and SWC (labeled as 404). The high voltage analog switch 102 further includes gate drivers for the output switches SWA, SWB, and SWC, which are labeled as 405-407, respectively. The output switch gate driver circuits 405-407, a clamp gate driver 401, and other components of the high voltage analog switch 102 can be controlled by the logic control and signal processing circuit 101 or other control circuit.

In one embodiment, the output switches SWA, SWB, and SWC are the same except that the output switch SWA additionally includes a clamp circuit comprising a transistor M3A and the clamp gate driver 401 for driving the transistor M3A. In addition, the transistors of the output switch SWC do not necessarily have to be high voltage transistors.

In the example of FIG. 4, the transistors M1A and M2A of the output switch SWA are high voltage N-channel metal oxide semiconductor field effect transistors (MOSFETs), i.e., NMOS transistors, that form an analog switch. In the example of FIG. 4, the source of the transistor M1A is coupled to the source of the transistor M2A and the gate of the transistor M1A is coupled to the gate of the transistor M2A. The anode of the Zener diode D1A is coupled to the sources of the transistors M1A and M2A and the anode of the Zener diode D2A is coupled to the gates of the transistors M1A and M2A. The cathodes of the Zener diodes D1A and D2A are tied together. The Zener diodes D1A and D2A limit high voltages to protect the gate-to-source oxide of the transistors M1A and M2A. The output of the gate driver 405 is coupled to the gates of the transistors M1A and M2A to OPEN or CLOSE the output switch SWA. The output switches SWB and SWC can have the same components and operate in the same manner.

In the example of FIG. 4, the end node SWin is coupled to a drain of the transistor M1A and a drain of the transistor M2A is coupled to a drain of a transistor M1C of the output switch SWC. A drain of the transistor M2C of the output switch SWC is coupled to the end node SWout. A drain of the transistor M1B of the output switch SWB is coupled to the drains of the transistors M2A and M1C. A drain of the transistor M2B of the output switch SWB is coupled to ground.

When the high voltage analog switch 102 is ON, the transistors M1A and M2A are driven by the output switch gate driver circuit 405 to be ON, the transistors M1C and M2C are driven by the output switch gate driver circuit 407 to be ON, and the transistors M1B and M2B are driven by the output switch gate driver circuit 406 to be OFF. When the high voltage analog switch 102 is OFF, the transistors M1A and M2A are driven by the output switch gate driver circuit 405 to be OFF, the transistors M1C and M2C are driven by the output switch gate driver circuit 407 to be OFF, and the transistors M1B and M2B are driven by the output switch gate driver circuit 406 to be ON.

In the example of FIG. 4, the output switch SWA further includes the transistor M3A, which is connected across the gate-to-source voltage of the transistors M1A and M2A. More specifically, the source of the transistor M3A is coupled to the sources of the transistors M1A and M2A and the drain of the transistor M3A is coupled to the gates of the transistors M1A and M2A. When the output switch SWA is OPEN, the transistor M3A is driven by the clamp gate driver 401 to be ON to shunt the gate and source voltages of the transistors M1A and M2A to 0V to ensure that the transistors M1A and M2A remain OFF. That is, the transistor M3A keeps the output switch SWA OPEN when the high voltage analog switch 102 is OFF.

Figure 5:
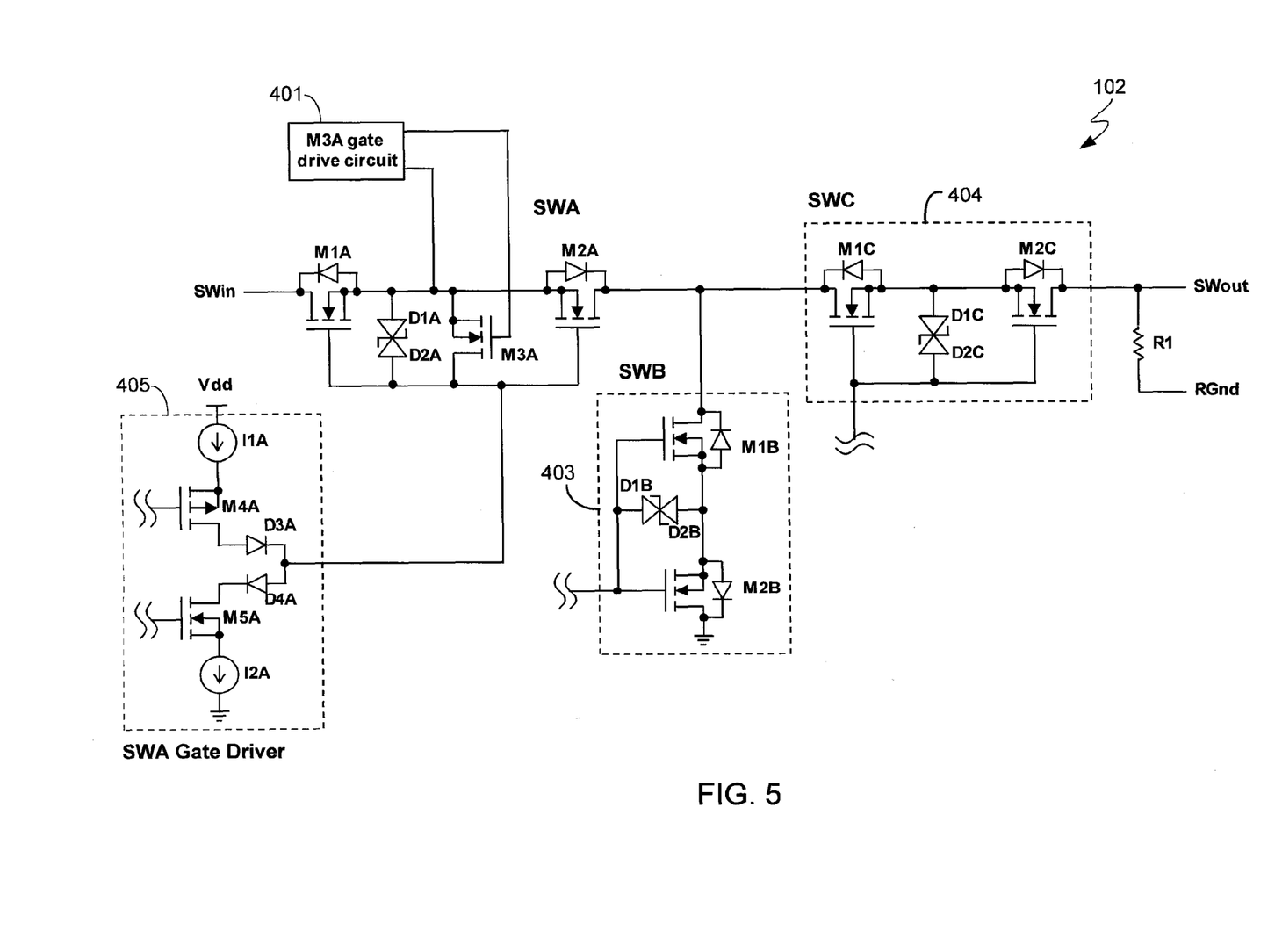
FIG. 5 shows a schematic diagram of an output switch gate driver circuit of a high voltage analog switch in accordance with an embodiment of the present invention.

FIG. 5 shows a schematic diagram of an output switch gate driver circuit (e.g., 405, 406, or 407) of a high voltage analog switch 102 in accordance with an embodiment of the present invention. FIG. 5 shows further details of the output switch gate driver circuit 405 for driving the output switch SWA, but the same output switch gate driver circuit may be employed to drive the output switch SWB or SWC. In one embodiment, the output switch gate driver circuits for the output switches SWA, SWB, and SWC are the same. The output switch gate driver circuits 406 and 407 for the output switches SWB and SWC, respectively, are not shown in FIG. 5 for clarity of illustration.

In the example of FIG. 5, the output switch gate driver circuit 405 comprises PMOS transistor M4A and NMOS transistor M5A, diodes D3A and D4A, and current sources I1A and I2A. The sources of the transistors M4A and M5A are coupled to the current sources I1A and I2A, respectively. The drain of the transistor M4A is coupled to the anode of the diode D3A, the drain of the transistor M5A is coupled to the cathode of the diode D4A. The anode of the diode D4A is coupled to the cathode of the diode D3A at an output node that drives the output switch SWA, i.e., the gates of the transistors M1A and M2A.

For medical ultrasound applications, the voltages at the end nodes SWin and SWout are at 0V before the high voltage analog switch 102 changes state from ON to OFF or from OFF to ON. To close the output switch SWA, the transistor M4A is turned ON to charge the gates of the transistors M1A and M2A to Vdd minus one diode drop from the diode D3A. The supply voltage Vdd coupled to the current source I1A can be +10V, for example. The charging current is limited by the current source I1A, which can be around 2 mA. The Zener voltage for Zener diodes D1A and D2A of the output switch SWA is greater than the supply voltage Vdd so there is no current flowing through the Zener diodes D1A and D2A, as that would run a risk of adding current noise. Once the gate capacitance of the transistors M1A and M2A has been charged close to the supply voltage Vdd, there is no more current flow. When the transducer excitation signal from a transmitter TX ramps up from 0V to +100V on the end node SWin, the source voltage on the transistors M1A and M2A will also ramp to +100V. The gate voltage of the transistors M1A and M2A will ramp up to +100V plus Vdd minus a small drop from the diode D3A. The diode D3A is reverse biased at that point.

The gate-to-source capacitances of the transistors M1A and M2A are holding the gate charge voltage to keep the transistors M1A and M2A ON. After 500 ns or less, the transducer excitation signal will ramp down from +100V to −100V. The sources of the transistors M1A and M2A will also ramp down to −100V. The voltage on the gates of the transistors M1A and M2A will ramp down to −100V plus Vdd minus a small drop from the diode D3A. The diode D3A is forward biased at that point. The current set by the current source I1A flows through the transistor M4A to the diode D3A to the Zener diode D2A to the Zener diode D1A to −100V. The gate-to-source voltage Vgs of the transistors M1A and M2A is limited by the back-to-back Zener diodes D1A and D2A. After another 500 ns, the transducer excitation signal returns to ground.

To open the output switch SWA, the transistor M5A is turned ON to discharge the gates of the transistors M1A and M2A to 0V plus one diode drop from the diode D4A. Discharging current is limited by the current source I2A, which can be 2 mA. Once the gate capacitance of the transistors M1A and M2A has been discharged close to 0V, there is no more current flow. When the transducer excitation signal ramps up from 0V to +100V on the end node SWin, the source voltage on the transistors M1A and M2A will stay close to 0V. The gate voltage of the transistors M1A and M2A also will be close to 0V, keeping the transistors M1A and M2A OFF. The transistor M3A is turned ON to ensure that the transistors M1A and M2A stay OFF by shunting their gate and source terminals together. When the transducer excitation signal ramps down to −100V, the sources of the transistors M1A and M2A will ramp to −100V plus one diode drop due to the body diode of the transistor M1A. The gate voltage of the transistors M1A and M2A is also at −100V plus one diode drop because the transistor M3A is ON. The diode D4A is now reversed biased at that point; there is no current flow and the transistors M1A and M2A remain off.

Figure 6:
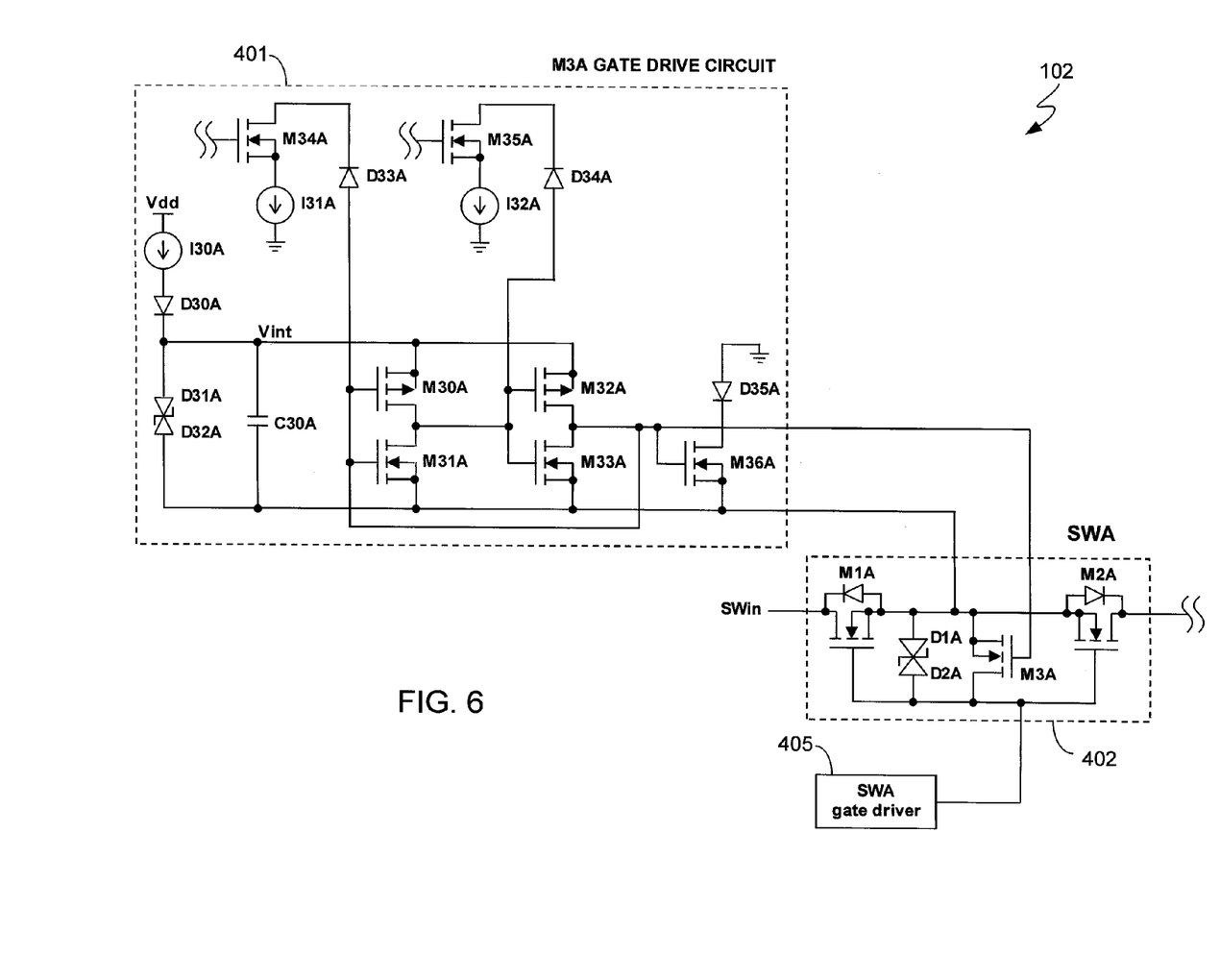
FIG. 6 shows a schematic diagram of a clamp gate driver circuit of an output switch in accordance with an embodiment of the present invention.

FIG. 6 shows a schematic diagram of a clamp gate driver 401 for driving the transistor M3A of a high voltage analog switch 102 in accordance with an embodiment of the present invention. FIG. 6 also shows the output switch SWA (see 402) and the outputs switch gate driver circuit 405 for the output switch SWA.

In the example of FIG. 6, the current source 130A, diode D30A, Zener diode D31A, Zener diode D32A, and capacitor C30A generate an internal floating supply voltage Vint that is referenced to the source terminals of the transistors M1A and M2A. The sources of the transistors M30A and M32A are coupled to the internal floating supply voltage Vint and the sources of the transistors M31A and M33A are coupled to the sources of the transistors M1A and M2A. The drains of the transistors M30A and M31A are coupled to the gates of the transistors M32A and M33A. The drains of the transistors M32A and M33A are coupled to drive the gate of the transistor M3A.

The current from the current source 130A flows through the diode D30A to charge the capacitor C30A through the sources of the transistors M1A and M2A then through the body diode of the transistor M1A to ground or through the body diode of the transistor M2A to ground. Zener diodes D31A and D32A limit the maximum voltage allowed to charge the capacitor C30A. The internal floating supply voltage Vint is used to power a CMOS (complementary metal oxide semiconductor) latch consisting of the transistors M30A, M31A, M32A, and M33A. The transistors M30A and M31A are configured as a first CMOS inverter. The transistors M32A and M33A are configured as a second CMOS inverter. The output of the first CMOS inverter (i.e., the drains of the transistors M30A and M31A) drives the input of the second CMOS inverter (i.e., the gates of the transistors M32A and M33A). The output of the second CMOS inverter (i.e., the drains of the transistors M32A and M33A) drive the input of the first CMOS inverter (i.e., the gates of the transistors M30A and M31A). This topology creates a latched cell, as the circuit can drive itself to maintain a stable logic state.

The state of the latched cell is controlled by turning the transistors M34A and M35A ON and OFF. When the transistor M35A is turned ON, the transistor M34A is OFF. The transistor M35A will pull the gates of the transistors M32A and M33A to ground through the diode D34A with a limited current defined by the current source I32A. This sets the gates of the transistors M32A and M33A to a logic LOW state. The drains of the transistors M32A and M33A will be at a logic HIGH state, driving the gates of the transistors M30A, M31A, M36A and M3A HIGH. The transistor M3A is turned ON, shunting the gate and source terminals of the transistors M1A and M2A together and keeping them OFF. The output switch SWA is thus held open. The drains of the transistors M30A and M31A will be at a logic LOW to keep the gates of the transistors M32A and M33A at a logic LOW level.

When the transistor M34A is turned ON, the transistor M35A is OFF. The transistor M34A will pull the gates of the transistors M30A and M31A to ground through the diode D33A with a limited current defined by the current source I31A. This sets the gates of the transistors M30A and M31A to a logic LOW state. The drains of the transistors M30A and M31A will be at a logic HIGH state driving the gates of the transistors M32A and M33A. The drains of the transistors M32A and M33A will be at logic LOW. The transistors M36A and M3A are OFF, allowing the output switch gate driver circuit 405 to close the output switch SWA.

As can be appreciated from the foregoing, the high voltage analog switches of the present invention can pass high voltage transducer excitation signals without necessarily needing a high voltage power supply. For example, the supply voltage VDD and all other supply voltages of the analog switches can be +/−10V or less.

High voltage analog switches have been disclosed. While specific embodiments of the present invention have been provided, it is to be understood that these embodiments are for illustration purposes and not limiting. Many additional embodiments will be apparent to persons of ordinary skill in the art reading this disclosure.

What is claimed is:

1. A high voltage analog switch comprising:
a first output switch comprising a first node coupled to a first end node of the high voltage analog switch and a second node coupled to a first node of a second output switch, the first end node of the high voltage analog switch being coupled to receive a high voltage transducer excitation signal, the first output switch including a clamp circuit that keeps the first output switch open when the high voltage analog switch is OFF;
the second output switch comprising a second node coupled to a second end node of the high voltage analog switch, the second end node of the high voltage analog switch being coupled to a piezoelectric transducer; and
a third output switch comprising a first node coupled to the second node of the first output switch and the first node of the second output switch, the third output switch comprising a second node coupled to ground,
wherein the first and second output switches are closed and the third output switch is open to pass the high voltage transducer excitation signal from the first end node to the second end node of the high voltage analog switch when the high voltage analog switch is ON, and the first and second output switches are open and the third output switch is closed when the high voltage analog switch is OFF,
wherein the first output switch comprises a first transistor and a second transistor forming an analog switch, and
the clamp circuit comprises a third transistor having a first terminal, a second terminal, and a gate, the first terminal of the third transistor being coupled to a gate of the first transistor and a gate of the second transistor, the second terminal of the third transistor being coupled to a source of the first transistor and a source of the second transistor, and the third transistor is ON to shunt the gates and the sources of the first and second transistors together when the first output switch is open.

2. The high voltage analog switch of claim 1, wherein a source of the third transistor is coupled to the sources of the first and second transistors and a drain of the third transistor is coupled to the gates of the first and second transistors.

3. The high voltage analog switch of claim 1, wherein the clamp circuit further comprises a clamp gate driver circuit that drives the gate of the third transistor, the clamp gate driver circuit comprising a latched cell.

4. The high voltage analog switch of claim 3, wherein the latched cell comprises a first inverter and a second inverter, an output of the first inverter drives an input of the second inverter, an output of the second inverter drives an input of the first inverter, and the output of the second inverter drives the gate of the third transistor.

5. The high voltage analog switch of claim 4, wherein the first inverter comprises a fourth transistor and a fifth transistor and the second inverter comprises a sixth transistor and a seventh transistor, a source of the fifth transistor and a source of the seventh transistor being coupled to the sources of the first and second transistors and a drain of the sixth transistor and a drain of the seventh transistor being coupled to the gate of the third transistor.

6. The high voltage analog switch of claim 5, further comprising a current source and a capacitor, wherein current from the current source charges the capacitor to generate an internal supply voltage that is referenced to the sources of the first and second transistors.

7. A medical ultrasound device comprising:
a high voltage analog switch comprising a first end node and a second end node, the high voltage analog switch comprising a first output switch, a second output switch, and a third output switch, a first terminal of the first output switch being coupled to the first end node of the high voltage analog switch, a second terminal of the second output switch being coupled to the second end node of the high voltage analog switch, a first terminal of the third output switch being coupled to a second terminal of the first output switch and to a first terminal of the second output switch, a second terminal of the third output switch being coupled to ground, the high voltage analog switch further comprising a clamp circuit that keeps the first output switch open when the high voltage analog switch is OFF;
a transmitter/receiver pair being coupled to the first end node of the high voltage analog switch; and
a piezoelectric transducer coupled to the second end node of the high voltage analog switch to receive a high voltage transducer excitation signal transmitted by a transmitter of the transmitter/receiver pair through the high voltage analog switch when the high voltage analog switch is ON,
wherein the first and second output switches are closed and the third output switch is open to pass the high voltage transducer excitation signal from the first end node to the second end node of the high voltage analog switch when the high voltage analog switch is ON, and the first and second output switches are open and the third output switch is closed when the high voltage analog switch is OFF,
wherein the clamp circuit comprises a third transistor having a first terminal, a second terminal, and a gate, the first terminal of the third transistor being coupled to a gate of the first transistor and a gate of the second transistor, the second terminal of the third transistor being coupled to a source of the first transistor and a source of the second transistor, and the third transistor is ON to shunt the gates and the sources of the first and second transistors together when the first output switch is open.

8. The medical ultrasound device of claim 7, wherein the high voltage analog switch does not have a power supply that provides more than +/−10V.

9. The medical ultrasound device of claim 7, wherein the high voltage transducer excitation signal has a voltage of at least 80V peak-to-peak.

10. The medical ultrasound device of claim 7, wherein the first output switch comprises a first transistor and a second transistor.

11. The medical ultrasound device of claim 7, wherein a source of the third transistor is coupled to the sources of the first and second transistors and a drain of the third transistor is coupled to the gates of the first and second transistors.

12. The medical ultrasound device of claim 7, wherein the clamp circuit further comprises a clamp gate driver circuit that drives the gate of the third transistor, the clamp gate driver circuit comprising a latched cell.

13. The medical ultrasound device of claim 12, wherein the latched cell comprises a first inverter and a second inverter, an output of the first inverter drives an input of the second inverter, an output of the second inverter drives an input of the first inverter, and the output of the second inverter drives the gate of the third transistor.

14. A high voltage analog switch comprising:
a first output switch comprising a first node coupled to a transmitter/receiver pair, the first output switch comprising a first transistor and a second transistor forming a first analog switch, the first output switch further comprising a clamp circuit that keeps the first transistor and the second transistor OFF when the high voltage analog switch is OFF;

a second output switch comprising a first node coupled to a second node of the first output switch and a second node coupled to a piezoelectric transducer, the second output switch comprising a fourth transistor and a fifth transistor forming a second analog switch; and a third output switch comprising a first node coupled to the second node of the first output switch and to the first node of the second output switch, a second node of the third output switch being coupled to ground, the third output switch comprising a sixth transistor and a seventh transistor forming a third analog switch, wherein the first and second output switches are closed and the third output switch is open to pass a high voltage transducer excitation signal from a transmitter of the transmitter/receiver pair to the piezoelectric transducer when the high voltage analog switch is ON, and the first and second output switches are open and the third output switch is closed when the high voltage analog switch is OFF, wherein the clamp circuit comprises a third transistor having a first terminal, a second terminal, and a gate, the first terminal of the third transistor being coupled to a gate of the first transistor and a gate of the second transistor, the second terminal of the third transistor being coupled to a source of the first transistor and a source of the second transistor, and the third transistor is ON to shunt the gates and the sources of the first and second transistors together when the first output switch is open.

15. The high voltage analog switch of claim 14, wherein a source of the third transistor is coupled to the sources of the first and second transistors and a drain of the third transistor is coupled to the gates of the first and second transistors.

16. The high voltage analog switch of claim 14, wherein the high voltage analog switch does not have a power supply that provides a voltage that exceeds +/−10V.

17. The high voltage analog switch of claim 14, wherein the high voltage transducer excitation signal has a voltage of at least 80V peak-to-peak.

* * * * *